United States Patent [19]

Coatoam

[11] Patent Number: 5,246,370

[45] Date of Patent: Sep. 21, 1993

[54] DENTAL IMPLANT METHOD

[76] Inventor: Gary W. Coatoam, 110 Timbercove South, Longwood, Fla. 32779

[21] Appl. No.: 982,763

[22] Filed: Nov. 27, 1992

[51] Int. Cl.$^5$ .............................. A61C 8/00; A61C 5/00

[52] U.S. Cl. ................................... 433/173; 433/175; 433/215

[58] Field of Search ............... 433/172, 173, 174, 175, 433/176, 75, 76, 215

[56] References Cited

U.S. PATENT DOCUMENTS

| | | | |
|---|---|---|---|
| 4,244,689 | 1/1981 | Ashman | 433/175 |
| 4,360,343 | 11/1982 | Hussein | 433/173 |
| 4,998,881 | 3/1991 | Lanks | 433/76 X |
| 5,004,422 | 4/1991 | Propper | 433/175 |
| 5,015,183 | 5/1991 | Fenich | 433/76 |

*Primary Examiner*—Gene Mancene
*Assistant Examiner*—Nicholas D. Lucchesi
*Attorney, Agent, or Firm*—William M. Hobby, III

[57] ABSTRACT

A method of attaching a dental implant includes the making of a dental implant having the general shape and size to fit a bone cavity for a removed tooth plus a cylindrical extension prong to fit a drilled bore in the bottom of the cavity formed by the removed tooth. The dental implant also has a non-circular shaped opening in the top thereof with a threaded bore in the bottom of the opening for attaching an insert thereto. The method includes extracting a patient's tooth, selecting a drill guide having the general shape of the bone cavity from the removed tooth and having a bore therethrough, then passing a drill bit through the drill guide bore and drilling a bore in a predetermined position in the bottom portion of the bone cavity. The dental implant is selected of a predetermined size and anchored in the bone cavity. A temporary generally flat head insert is attached to the implant and is later replaced with the tooth holding insert and an artificial tooth attached thereto.

8 Claims, 2 Drawing Sheets

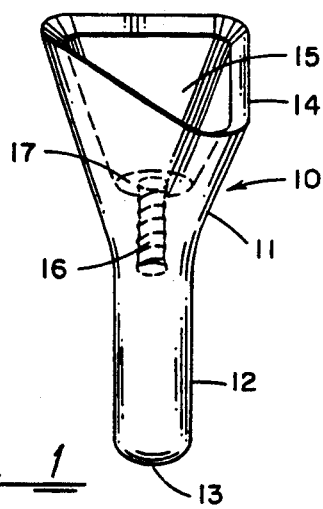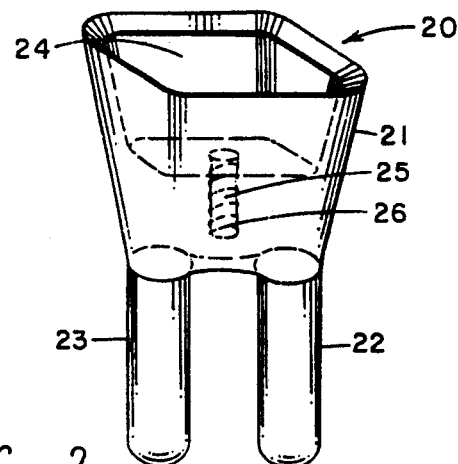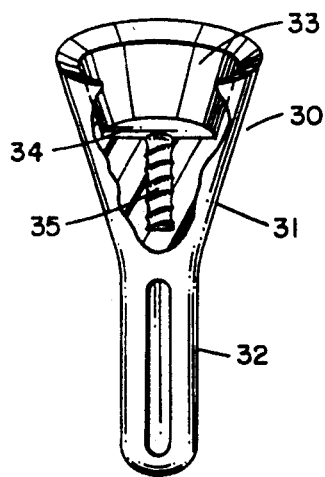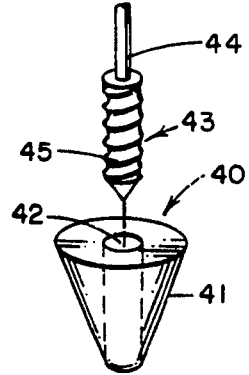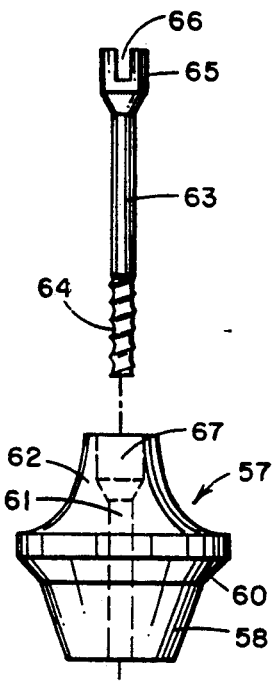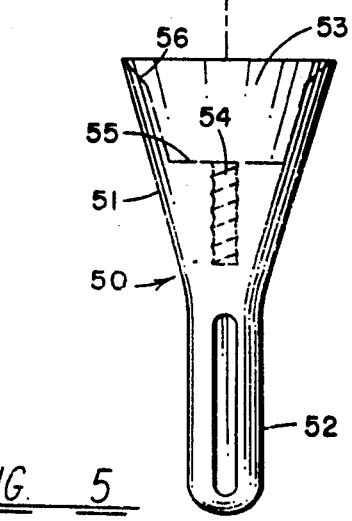

DENTAL IMPLANT METHOD

BACKGROUND OF THE INVENTION

The present invention relates to a method for placement of an endosseous implant into an extraction site of a patient.

There has been much research in recent years into handling damaged natural teeth which have been damaged through disease or accident by extracting the teeth and then immediately, or sometimes later, implanting an artificial root which has the same function as the original natural tooth and then attaching a tooth or other prosthetic device to the implanted artificial root.

In the past, various types of artificial teeth and other surgical implants have been developed for replacing teeth or other joints or bone portions. Originally, dental implants and other surgical implants were attached to a patient's bone using various adhesives, mechanically retentive surfaces composed primarily of titanium or titanium dioxide, and later surface coatings of various biologically compatible materials were developed in which the bone grows into and attaches to the implant. Porous materials alone have not always been sufficiently strong for dental implants so that it has been necessary to emplace a piece of solid material, such as metallic center post or rod, inside the porous material to form a surgical implant with a porous surface. Typically, implants and the prosthetic posts that subsequently inserted into implants have been circularly shaped at the point where the implant opens into the oral cavity so that it is possible to drill a circular hole with a conventional drill to precisely fit the cylindrical implant in the bone. Even in the case where new technology involving the use of guided tissue regeneration has been used, a cylindrical implant has been placed into a tooth socket, which is rarely circular at its exit opening. The current technology only delineates that the implant have a sufficiently porous, mechanical, or biological surface to allow the attachment of the bone thereto. A dental implant typically is implanted into bone in the approximate position of an extracted tooth and has a post or other attaching means extending from the top of the implant for attaching an artificial tooth. The inserts are commonly attached with a threaded fastener which threads through the insert into the supporting implant.

The present invention deals with a method of extracting a tooth and then implanting an artificial root and attaching an artificial tooth to the dental implant artificial root or anchoring means. Prior patents that show various types of artificial tooth root implanting and anchoring means may be seen in the Hakamatsuka et al., U.S. Pat. No. 4,713,006, for an artificial tooth root which is divided into a tooth group body and a root holder and in which the material for the artificial tooth root body is selected for its strength. In the Farris et al., U.S. Pat. No. 4,492,577, a surgical implant with a solid interior and porous surfaces is provided and is illustrated with a two-pronged shaped artificial root. In the Niznick U.S. Pat. No. Re. 33,796, a coping insert for use with a dental implant is illustrated in which a thermoplastic one-piece coping insert is adapted for use with a dental implant anchoring means. In the Hama et al., U.S. Pat. No. 4,818,559, a method for producing endosseous implants is provided which thermally sprays a ceramic material onto the surface of a metallic core for making implants for implantation into the bone for tooth roots and the like. In the Kawahara et al., U.S. Pat. No. 4,964,801, an endosseous implant having a polycapillary structure is provided for being set into the alveolar bone for use in dental prosthesis. In the Flanagan et al. U.S. Pat. No. 4,812,120, an implantable percutaneous device provides for a dental implant which has a metal core that is directly coated with layers of polymer.

In dental implants, various artificial root implants are manufactured in different shapes and materials so that when a tooth is removed from the bone, after the socket is healed, the bone can be drilled for insertion of an artificial root implant which may have a surface to allow the bone to attach thereto and may also be attached or filled with a composition to help the bone adhere to the artificial root implant. In the case where an implant is placed immediately at the time of extraction, the hole is deepened with a cylindrical drill, bone grafting material or guided tissue regeneration membranes are used to cover and surround the top portion of the implant to try to fill the void created by the discrepancy of the cylindrical implant shape in a non-cylindrical hole. The implant is then covered with a gingival flap. The root implant is then allowed to heal so that the bone grows into the porous or specially made surface to anchor the artificial implant to the bone so that at some later period, once the bone has adhered to the artificial root, a prosthetic insert can be attached to the root implant. An artificial tooth, or prosthetic locking attachment can then be attached to the prosthetic insert post with an adhesive or screw type attachment. It is common to attach the prosthetic insert post with a threaded fastener designed to fit a predrilled and threaded bore in the implant. Typically, both the implanted root and the insert have been made with cylindrical shapes so that the bone can be drilled with a cylindrical shape to make an exact fitting artificial root implant match the drilled bore. This has some advantages but makes it easier for the implanted artificial root as well as the insert to rotate or loosen when certain types of pressure are placed on the artificial implant and tooth. It also dictates that the exit shape from the gingiva be circular rather than tooth shaped, thereby adversely affecting the esthetics and manageability of the ultimate prosthetic design.

The present invention utilizes a method and a dental implant which deliberately avoids cylindrical and round shapes in the dental implant as well as in the artificial tooth insert so that when attached to a patient, a greater resistance to the rotation is provided against the breaking loose of the artificial implant by the use of a non-circular shape. It also provides for a more natural exit profile from the gingiva so as to render the implant and prosthetic insert post more acceptable for tooth replacement. Additionally, this invention provides a better design and shape for guided tissue regeneration when implants are placed immediately at the time of extraction of a natural tooth.

SUMMARY OF THE INVENTION

A method of attaching a dental implant includes the making of a dental implant having the general shape and size to fit a bone cavity for a removed tooth plus a cylindrical extension prong or prongs to fit a drilled bore extending laterally and/or apically beyond the dimensions of the cavity formed by the removed tooth. The dental implant also has a non-circular shaped opening in the top thereof with a threaded bore in the bottom of the opening for attaching an insert thereto. The method includes extracting a patient's tooth, selecting a drill guide having the general shape of the bone cavity from the removed tooth and having a bore therethrough, then passing a drill bit through the drill guide bore and drilling a bore in a predetermined position in the bottom portion of the bone cavity. The dental implant is selected of a predetermined size corresponding to the prepared osteotomy site and anchored in the bone cavity. A temporary generally flush head insert is attached to the implant and is later replaced with the tooth holding insert and an artificial tooth attached thereto.

BRIEF DESCRIPTION OF THE DRAWING

Other objects, features and advantages of the present invention will be apparent from the written description and the drawings in which:

FIG. 1 is a perspective view of a dental implant for use in accordance with the present invention;

FIG. 2 is a perspective view of a second embodiment of a dental implant;

FIG. 3 is a perspective view of a third dental implant in accordance with the present invention;

FIG. 4 is an exploded perspective view of a drill guide and drill bit for use with the present dental implant method;

FIG. 5 is an exploded view of a dental implant and the attaching of an artificial tooth supporting insert;

FIG. 6 is an exploded perspective view of a dental implant having a temporary flush head insert being attached thereto.

DETAILED DESCRIPTION OF THE PREFERRED EMBODIMENTS

Figure 7:
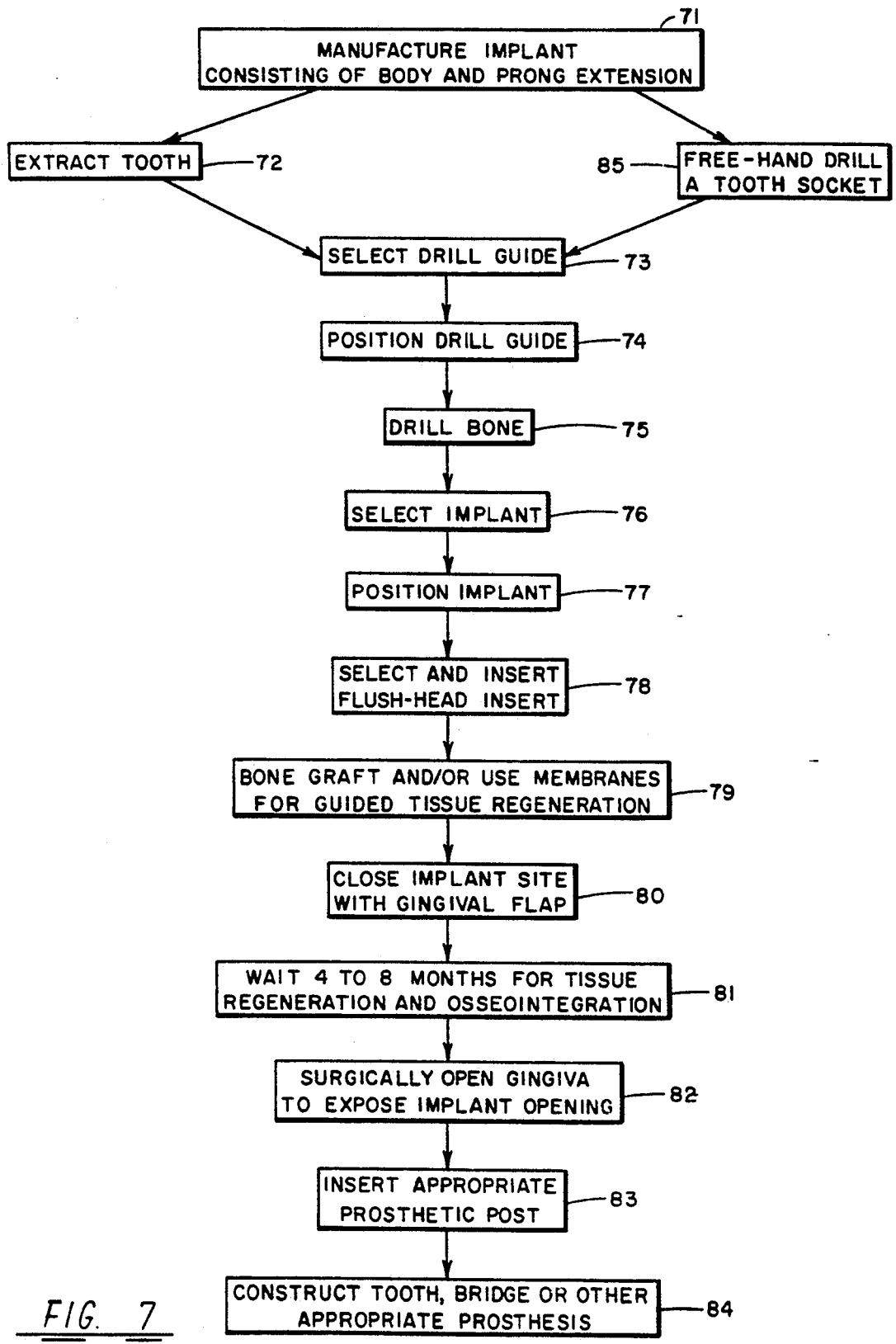
FIG. 7 is a flow diagram of a method in accordance with the present invention.

Referring to the drawings and especially to FIG. 1, an artificial root dental implant is shown having a generally triangular shaped body 11 having a cylindrical prong 12 protruding from the triangular shape and having a rounded bottom surface 13 and rounded corners 14. The root implant 10 has a generally triangular shaped opening 15 therein having a threaded bore 16 drilled in the bottom portion 17 of the opening 15. The triangular opening 15 has generally smooth corners. It is slightly convex in shape, from the base of the triangle to the apex of the triangle, corresponding to the slight convex shape of bone adjacent to the extraction site where this implant would be utilized. The main body portion 11 has been shaped in a generally triangular shape, corresponding to the approximate shape of a maxillary molar extraction site, to fit the cavity of a removed natural tooth from a patient while the supporting prong portion 12 has been shaped to fit a predetermined cylindrical drilled bore drilled into the bone.

FIG. 2 illustrates a second embodiment of a dental implant which has a more rectangular shaped main body 21 and a pair of protruding prongs 22 and 23 protruding from the bottom thereof. The shaped body 21 is generally shaped to fit into the cavity opening formed by a removed mandibular molar while the rods 22 and 23 are shaped to be inserted into bores drilled into the bone at predetermined positions. This implant may also have just one prong extending from the main body 21. The implant 20 has a non-circular and more rectangular opening 24 in the top thereof having a bottom 25 having a threaded bore 26 in the bottom thereof for anchoring an insert. The surfaces on prongs 22, 23, and on the main body 21 as well as the surfaces on the main body 11 of the root implant 10 and the prongs 12 may have a surface coating or a surface formed thereon which is sufficiently porous or shaped for the bone of a patient to grow into and attach to the implant 10 or 20.

FIG. 3 shows a different shaped implant 30 having a main body 31 of a generally ovoid shape along with a root prong 32 protruding from the bottom thereof similar to the embodiment of FIG. 1 but shaped slightly different for a different tooth and having a different shaped opening 33. The opening 33 has a bottom 34 and a threaded bore 35 extending thereinto. The opening 33 is of a generally ovate shape for inserting a matching insert which is anchored to the threaded bore 35. Besides being ovate in shape, it is also slightly convex to assimilate the shape of the bone adjacent to the extraction site.

Turning to FIG. 4, a drill guide 40 has a main shaped body 41 designed to fit the approximate shape of the upper portion of the extraction site of a natural tooth and corresponding in shape to the main body of the implant from which the extension prong extrudes and has a predetermined bore size 42 therethrough that corresponds to the prong. A drill bit 43 has a shank 44 and a cutting surface 45 shaped to exactly fit through the bore 42 for precisely aligning the drill to drill a hole in a predetermined position for receiving a root prong 12 as in the implant of FIG. 1 or a prong 32 as in the implant 30. A drill guide of the shape as shown in FIG. 2 would have a pair of bores 42 for a drill guide shaped similar to the implant body 21. This drill guide can also have a contra-angled handle attached to it for ease of manipulation during fitting or drilling procedures. The drill guide can then be inserted into the cavity of the removed tooth and the bore drilled. Predetermined markings on the drill bit can indicate the depth of the drilled bore and could be varied so as to correspond to implants with the same body shape but varied prong length.

Referring to FIG. 5, a dental implant 50 has a non-round shape 51, such as the root implant shown in FIGS. 1 and 3, and has a prong 52 which is cylindrical shaped and an opening in the top 53 having a threaded bore 54 extending into the bottom 55 of the opening 53. The opening 53 top has angular or mitered surfaces 56 for fitting a matching insert 57. The insert 57 has a non-circular portion 58 exactly shaped to fit the opening 53 of an annular ledge 60 to exactly fit the angled surfaces 56. The insert 57 has a cylindrical bore 61 extending therethrough through the top portion 62 which is shaped like a tooth prepared for a crown and the attaching portion 58 and a threaded locking fastener 63 passes through the bore 61 and has its threaded portion 64 threadedly attached in the bore 54. Threaded fastener 63 has an enlarged head 65 with an opening 66 for a Phillips screwdriver, hex wrench or for a slot-type screwdriver or the like to thread the fastener 63 into the bore 54 while the insert 57 has an opening 67 for exactly matching the enlarged head 65. Top portion 62 of the insert 57 is the anchoring post for anchoring an artificial tooth which may be adhesively attached once the insert 57 is anchored to the implant 50.

Referring to FIG. 6, the implant 50 is shown having an enlarged, tooth-shaped portion 51 extending from the cylindrical prong 52 but having a temporary flush headed insert 68 anchored thereto with a flat headed threaded fastener 69. Temporary insert 68 is put in place after the root implant 50 has been implanted into a newly removed tooth section to give a gently rounded, but flush top surface 70 while the tooth area is healing and while the bone is growing into the surface of the implant for anchoring the implant into the bone. This cover cap 68 has the same non-cylindrical dimension of the implant opening, as well as having a corresponding convex shape.

FIG. 7 is a flow diagram of a process for anchoring the implants of FIGS. 1-3. An implant, according to FIGS. 1-3, is made in the first step (71) having a body portion to fit the removed tooth cavity along with cylindrical prongs extending therefrom, then extracting the tooth (72) from the patient or creating a similar extraction site (85) using free-hand technique and a dental drill and selecting a drill guide (73), such as the drill guide 41 of FIG. 4, positioning (74) the selected drill guide in the cavity left by the removed tooth or free-handed drilled site. The drill bit is then placed 43 in the bore 42 of the guide 41 to align the drill in the exact position for drilling a bore for attaching the implant. The bone is then drilled (75) in the patient in the bottom of the cavity to enlarge and make a cylindrical root portion of the removed tooth cavity. If the bone is part hard, the bored hole will be made in a series of steps using several drill guides with identical body shapes but increased drill opening diameters and using corresponding drill bits until the final diameter and length of the predetermined implant prong is realized.

An implant in accordance with FIGS. 1-3 is selected (76) which implant has the non-circular body portions which are shaped to fit a portion of the cavity formed by the removed tooth and which also has the non-circular insert holding portions in the top of the implant for holding an insert therein. The implant is positioned in the cavity (77) with the cylindrical shaped prong inserted thereinto and the non-cylindrical shape body portion of the insert forming a close match for the formed cavity. A flush headed insert, as shown in FIG. 6, is selected (78) and attached to the surgical implant, unless the implant comes prepackaged with the flush insert already in place. Guided tissue regeneration (79) is instituted by placing bone graft material and appropriate barrier membranes. The surgical site is closed (80) for an appropriate period of time to achieve osseointegration of the implant, which ususally takes about four months in the mandible and eight months in the maxilla. A surgical opening (82) is made to expose the flush headed insert, and the insert 68 of FIG. 6 is removed and replaced (83) with the tooth mounting post or insert 57 having the mounting post 62 which is threaded in place with the threaded fastener 63 attached in the threaded bore 54 by inserting a non-circular post portion 58 into a non-circular and matching opening 53 so that it will not rotate while attaching the threaded fastener 63 or after being fastened to the implant 50 of FIG. 5. Once the insert 57 is attached, an artificial tooth made to match the patient's tooth can be attached to the post portion 62 of FIG. 5 with an adhesive so that the implant and artificial tooth can be attached in a more secure fashion with greater support against rotation of the attached insert and post as well as the implant itself.

It should be clear at this time that a dental implant has been provided which, along with a method of attaching the implant and the inserts into the implants provides greater strength against the breaking loose or rotation of the implants or attached inserts. It should also be clear that the inserted prosthetic post will have a shape much more like that of a natural tooth when it has been prepared to receive an artificial tooth crown. Additionally, it should be clear that the tooth extraction socket will require less bone grafting to close any residual defect caused by the disparity in shape between a cylindrical implant and a tooth shaped socket. However, the present invention is not to be construed as limited to the forms shown which are to be considered illustrative rather than restrictive nor should it be considered as restricted in use to those methods described herein, which are considered only guidelines to the doctor placing the implant and prosthetic devices.

I claim:

1. A method of attaching a dental implant comprising the steps of:

extracting a patient's tooth;

selecting a drill guide having a shape of the general shape of the bone cavity from the removed tooth and having a bore therethrough;

placing the selected drill guide in the bone cavity;

passing a drill bit through said drill guide bore and drilling into said patient's bone in the bottom portion of said bone cavity;

selecting a dental implant to fit the bone cavity formed by the removed tooth and drilled portion;

anchoring the implant in the bone cavity;

attaching a temporary generally flathead insert in said implant; and replacing said temporary insert with a tooth insert; whereby an improved dental implant is attached in a bone cavity.

2. A method of attaching a dental implant in accordance with the method of claim 1 including the step of making an implant of predetermined shape and size having the same general nonuniform shape of a removed tooth bone cavity, with a cylindrical prong extending therefrom.

3. A method of attaching a dental implant in accordance with the method of claim 2 including the step of making a dental implant having an insert opening in the implant top of a non-circular shape for mounting an insert thereinto.

4. A method of attaching a dental implant in accordance with the method of claim 3 including the step of making a drill guide of predetermined shape and size having a predetermined bore therethrough.

5. A method of attaching a dental implant comprising the steps of:

making a dental implant having a general shape of a bone cavity from a removed tooth and with an elongated extension shaped to fit a drilled portion and having an open top having a nonuniform shape and at least one threaded bore in the bottom of said implant open top;

extracting a patient's tooth;

selecting a drill guide having a shape of the general shape of the bone cavity from the removed tooth and having a bore therethrough;

placing the selected drill guide in the bone cavity;

passing a drill bit through said drill guide bore and drilling into said patient's bone in the bottom portion of said bone cavity; and anchoring the implant in the bone cavity, whereby an improved dental implant is attached in a bone cavity.

6. A method of attaching a dental implant in accordance with the method of claim 5 including the step of selecting a flat headed insert shaped to fit into the dental implant open top and attaching the insert thereto.

7. A method of attaching a dental implant in accordance with the method of claim 6 including the step of removing said flat headed insert and attaching an artificial tooth mounting insert thereto having one end shaped to fit said dental implant opening.

8. A method of attaching a dental implant in accordance with the method of claim 7 including the step of mounting an artificial tooth to said dental implant insert.

* * * * *